United States Patent
McLaughlin et al.

(10) Patent No.: US 10,222,461 B2
(45) Date of Patent: *Mar. 5, 2019

(54) PHASE INVERSION ULTRASONIC IMAGING

(75) Inventors: Glen McLaughlin, Saratoga, CA (US); Ting-Lan Ji, San Jose, CA (US)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 895 days.

This patent is subject to a terminal disclaimer.

(21) Appl. No.: 11/926,068

(22) Filed: Oct. 28, 2007

(65) Prior Publication Data

US 2008/0103394 A1    May 1, 2008

Related U.S. Application Data

(63) Continuation of application No. 10/772,926, filed on Feb. 4, 2004, now Pat. No. 7,699,781, which is a
(Continued)

(51) Int. Cl.
*A61B 8/08*    (2006.01)
*A61B 5/00*    (2006.01)
(Continued)

(52) U.S. Cl.
CPC ............ *G01S 7/52077* (2013.01); *A61B 5/02* (2013.01); *G01S 7/52038* (2013.01);
(Continued)

(58) Field of Classification Search
CPC ......... A61B 5/7232; A61B 8/13; A61B 8/488; A61B 8/5207; A61B 8/5223; A61B 8/00;
(Continued)

(56) References Cited

U.S. PATENT DOCUMENTS 4,357,709 A * 11/1982 Butler et al. .................... 455/20
4,572,203 A    2/1986 Feinstein
(Continued)

FOREIGN PATENT DOCUMENTS

JP    09-131344    5/1997

OTHER PUBLICATIONS

W. Wilkening, et al., "Phase-Coded Pulse Sequence for Non-Linear Imaging," IEEE Ultrasonics Symposium 2000.
(Continued)

*Primary Examiner* — Jennifer Dieterle
*Assistant Examiner* — Vani Gupta
(74) *Attorney, Agent, or Firm* — Polsinelli LLP; Kory D. Christensen

(57) ABSTRACT

A system for ultrasonic imaging utilizing multiple sets of transmit pulses differing in amplitude, frequency, phase, and/or pulse width. One embodiment has phase differences between the k transmit signal as $$\frac{360}{k}$$

degrees providing for constructive interference of the $k^{th}$ order harmonic pulse, while an amplitude modulation of each transmit profile is constant between sets. These sets of pulses are transmitted into media of interest and received echoes from these pulses are combined to form an averaged signal. The averaged pulses represent the net common mode signal received from each of the transmit sets. This combined signal set is used to reconstruct an ultrasound image based on broad beam reconstruction methodology.

59 Claims, 6 Drawing Sheets

Related U.S. Application Data continuation of application No. 09/872,541, filed on May 31, 2001, now Pat. No. 6,866,631.

(51) Int. Cl.
*A61B 5/02* (2006.01)
*A61B 8/00* (2006.01)
*G01S 7/52* (2006.01)
*G01S 15/10* (2006.01)
*G01S 15/89* (2006.01)

(52) U.S. Cl.
CPC ...... *G01S 15/8959* (2013.01); *G01S 15/8963* (2013.01); *A61B 5/7257* (2013.01); *A61B 8/00* (2013.01); *A61B 8/485* (2013.01); *A61B 8/488* (2013.01); *A61B 8/5207* (2013.01); *A61B 8/5223* (2013.01); *A61B 8/5238* (2013.01); *G01S 7/52026* (2013.01); *G01S 15/104* (2013.01)

(58) Field of Classification Search
CPC ......... A61B 8/7257; A61B 5/02; A61B 8/485; A61B 8/5238
USPC ............ 600/454, 437, 443, 447, 458; 367/7; 702/39, 48, 49, 66, 67, 70, 76
See application file for complete search history.

(56) References Cited

U.S. PATENT DOCUMENTS

| | | | |
|---|---|---|---|
| 4,630,305 A * | 12/1986 | Borth .................. | G10L 21/0208 381/317 |
| 4,691,326 A * | 9/1987 | Tsuchiya ............ | H04B 1/70712 375/152 |
| 4,764,013 A * | 8/1988 | Johnston ....................... | 356/484 |
| 4,803,990 A | 2/1989 | Bonnefous et al. | |
| 4,917,097 A * | 4/1990 | Proudian et al. ............. | 600/463 |
| 5,033,019 A * | 7/1991 | White ................... | G06F 17/142 708/321 |
| 5,119,342 A | 6/1992 | Harrison, Jr. et al. | |
| 5,135,000 A | 8/1992 | Akselrod et al. | |
| 5,140,558 A | 8/1992 | Harrison, Jr. et al. | |
| 5,224,481 A | 7/1993 | Ishihara et al. | |
| 5,233,993 A | 8/1993 | Kawano | |
| 5,241,473 A | 8/1993 | Ishihara et al. | |
| 5,255,683 A | 10/1993 | Monaghan | |
| 5,278,757 A | 1/1994 | Hoctor et al. | |
| 5,291,090 A | 3/1994 | Dias | |
| 5,295,485 A | 3/1994 | Shinomura et al. | |
| 5,302,372 A | 4/1994 | Lin et al. | |
| 5,349,524 A | 9/1994 | Daft et al. | |
| 5,410,516 A | 4/1995 | Uhlendorf et al. | |
| 5,453,575 A | 9/1995 | O'Donnell et al. | |
| 5,456,257 A | 10/1995 | Johnson et al. | |
| 5,483,963 A | 1/1996 | Butler et al. | |
| 5,505,203 A | 4/1996 | Deitrich et al. | |
| 5,632,277 A | 5/1997 | Chapman et al. | |
| 5,667,373 A * | 9/1997 | Wright et al. ................ | 600/443 |
| 5,722,412 A | 3/1998 | Pflugrath et al. | |
| 5,740,806 A | 4/1998 | Miller | |
| 5,793,701 A | 8/1998 | Wright et al. | |
| 5,817,024 A | 10/1998 | Ogle et al. | |
| 5,839,442 A | 11/1998 | Chiang et al. | |
| 5,893,363 A | 4/1999 | Little et al. | |
| 5,897,501 A | 4/1999 | Wildes et al. | |
| 5,904,652 A | 5/1999 | Gilbert et al. | |
| 5,905,692 A | 5/1999 | Dolazza et al. | |
| 5,910,999 A * | 6/1999 | Mukohzaka ......... | A61B 5/1172 382/124 |
| 5,921,931 A * | 7/1999 | O'Donnell ............... | A61B 8/06 382/162 |
| 5,925,967 A | 7/1999 | Toda | |
| 5,970,025 A | 10/1999 | Cole et al. | |
| 5,973,438 A | 10/1999 | Toda | |
| 6,023,977 A | 2/2000 | Langdon et al. | |
| 6,055,861 A | 5/2000 | Banta, Jr. et al. | |
| 6,056,693 A | 5/2000 | Haider | |
| 6,089,096 A | 7/2000 | Alexandru | |
| 6,102,859 A * | 8/2000 | Mo ......................... | A61B 8/00 600/443 |
| 6,108,572 A | 8/2000 | Panda et al. | |
| 6,113,545 A | 9/2000 | Chiao et al. | |
| 6,120,448 A | 9/2000 | Bradley et al. | |
| 6,132,377 A | 10/2000 | Boloforosh et al. | |
| 6,135,961 A | 10/2000 | Pflugrath et al. | |
| 6,139,498 A | 10/2000 | Katsman et al. | |
| 6,139,501 A | 10/2000 | Roundhill et al. | |
| 6,155,981 A | 12/2000 | Ermert et al. | |
| 6,168,656 B1 | 1/2001 | Napolitano | |
| 6,174,286 B1 | 1/2001 | Ramamurthy et al. | |
| 6,193,662 B1 | 2/2001 | Hwang | |
| 6,193,663 B1 | 2/2001 | Napolitano et al. | |
| 6,203,498 B1 | 3/2001 | Bunce et al. | |
| 6,206,833 B1 | 3/2001 | Christopher | |
| 6,210,334 B1 | 4/2001 | Phillips | |
| 6,213,951 B1 | 4/2001 | Kirshnan et al. | |
| 6,221,018 B1 | 4/2001 | Ramamurthy et al. | |
| 6,238,346 B1 | 5/2001 | Mason | |
| 6,251,073 B1 | 6/2001 | Imran et al. | |
| 6,371,914 B1 * | 4/2002 | Arditi ..................... | A61B 8/481 600/443 |
| 6,406,430 B1 * | 6/2002 | Ishrak ................. | G01S 7/52039 600/441 |
| 6,506,158 B2 * | 1/2003 | Kawagishi et al. .......... | 600/443 |
| 6,524,252 B1 | 2/2003 | Yu et al. | |
| 6,638,230 B2 * | 10/2003 | Brock-Fisher ................ | 600/458 |
| 7,226,416 B2 * | 6/2007 | McLaughlin et al. ........ | 600/443 |
| 7,396,336 B2 * | 7/2008 | Orszulak et al. .................. | 601/2 |
| 7,699,781 B2 * | 4/2010 | McLaughlin et al. ........ | 600/443 |
| 7,758,508 B1 * | 7/2010 | Thiele ..................... | A61B 8/467 600/440 |
| 2004/0059225 A1 * | 3/2004 | Hao et al. ...................... | 600/458 |
| 2006/0018289 A1 * | 1/2006 | Schulist ................ | H04W 52/50 370/335 |

OTHER PUBLICATIONS

Wilkening, W. et al., "Phase-Coded Pulse Sequence for Non-Linear Imaging." Ultrasonics Symposium, 2000 IEEE, Issued Oct. 2000, vol. 2, pp. 1559-1562.

* cited by examiner

PHASE INVERSION ULTRASONIC IMAGING

CROSS-REFERENCE TO RELATED APPLICATIONS

This application is a continuation and claims the priority benefit of U.S. patent application Ser. No. 10/772,926 filed Feb. 4, 2004 now U.S. Pat. No. 7,699,781 and entitled "System for Phase Inversion Ultrasonic Imaging," which is a continuation and claims the priority benefit of U.S. patent application Ser. No. 09/872,541 filed May 31, 2001 now U.S. Pat. No. 6,866,631 and entitled "Method for Phase Inversion Ultrasonic Imaging." The subject matter of this application is incorporated herein by reference.

This application is related to commonly owned U.S. patent application Ser. No. 10/226,843 filed Aug. 21, 2002 and entitled "Method for Phase Inversion Ultrasonic Imaging," which is a divisional patent application of U.S. patent application Ser. No. 09/872,541. The subject matter of this application is incorporated herein by reference.

BACKGROUND OF THE INVENTION

1. Field of the Invention

The present invention relates to ultrasound imaging, and more particularly, to a system for improving and enhancing ultrasound images.

Description of the Background Art

Ultrasonic imaging is frequently used for a variety of diagnostic procedures due to its non-invasive nature, low cost, and fast response time. These qualities are especially true in medical fields where the added benefit is reducing or eliminating a patient's exposure to radiation. Typically, ultrasound imaging is accomplished by 1) generating and directing an ultrasonic beam into media under investigation; and 2) observing any resulting waves that are reflected back from dissimilar tissues and tissue boundaries within that area. The resulting waves are received as signals. These received signals are then post-processed and imaged on a screen by plotting a spot whose intensity is proportional to the amplitude of a reflected beam from a given location. Determination of location is based upon a known transmission and re-radiation rate after the ultrasonic wave is pulsed into the media under investigation.

Typically, an ultrasonic signal transmitted into the media under investigation includes a burst of sinusoidal waves of a given waveform. These sinusoidal waves are applied to a transducer and form a transmitted signal. The transmitted signal is typically in the range of 40 kHz to 50 MHz, but more commonly, in the range of 40 kHz to 1 MHz. As the transmitted signal interacts with tissue layers and boundaries between layers, the ultrasonic signal is modified by being scattered, resonated, attenuated, reflected, or transmitted.

Media under investigation are often a non-linear media such as those commonly found in the human body. Non-linear media produce harmonic frequencies in the echoed signals. These additional frequency components continue to re-radiate through and, in turn, reflect off or interact with other structures. A portion of the reflected (or echoed) signals propagates back to a receiving transducer.

Fundamental and harmonic frequencies that are impinged upon a receiving transducer includes the full signal, which must then be further processed to eliminate noise and extraneous components. The receiving transducer may be the same as a transmitting transducer, or can be completely independent. When the same transducer is used, a transmit/receive (T/R) switch connects the transducer to either the transmitter electronics or the receiver post-processing electronics. The receiving transducer accepts the echo signal plus any generated noise and furnishes these to a portion of the post-processing electronics known as a beam former. Beam formers reject noise and have either an adaptive or fixed configuration. Adaptive beam formers are designed to reject variable directional noise sources by monitoring the noise field and adjusting internal parameters to minimize the background noise. Fixed beam formers are designed to reject isotropic noise and take advantage of the directional property of the reflected signal.

Ultimately, ultrasonic images of the human body are a product of harmonic imaging. Harmonic imaging is generally associated with either visualization of tissue boundaries and densities of different media, or imaging contrast agents at harmonic frequencies. Contrast agents are typically fluid filled micro-spheres that resonate at ultrasonic frequencies. Such agents are injected into the blood stream and are carried to various parts of the body. Once these agents are pulsed at ultrasonic frequencies, harmonic echo-locator signals are generated due to the resonance produced within the micro-spheres.

While ultrasonic procedures have a distinct number of advantages over other types of diagnostic techniques, prior art methods and systems have noise problems that make it difficult to determine the exact location and proper interpretation of the received signal. Various forms of averaging techniques have been employed to reduce the noise, but averaging alone is ineffective in locating images of interest between tissues with similar densities. (Echoed signals from tissues with similar densities will indicate a uniform mass with indistinct boundaries. Averaging won't help in this situation.) These interpretation difficulties are exacerbated by the fact that many tissues in the human body have similar densities. Therefore, a method and system are needed that can effectively overcome the stated difficulties while not negating the positive benefits of ultrasound imaging systems in general.

SUMMARY OF THE INVENTION

The present invention is a system and method for generating enhanced ultrasonic images. The invention utilizes multiple ultrasonic pulses that are transmitted in an alternating fashion into media of interest. These media being imaged may be a human body or some other linear and/or non-linear media. The ultrasonic pulses are modulated in a way that may vary in amplitude, frequency, phase, or pulse width. Each set of ultrasonic pulses is out-of-phase with other ultrasonic pulses by $$\frac{360°}{k},$$

where k is the number of pulse sets in the pulse sequence for a given transducer element number, n. An out-of-phase condition is a property when waveforms are of the same frequency but do not have corresponding intensity values at the same instant. The echo signals generated by the non-linear media interacting with these out-of-phase signals are measured and appropriately combined.

The present invention is based on the observation that many types of media scatter sound in a non-linear manner. With an ultrasonic imaging system based on linear-scattering media, the return signal is a time-shifted, amplitude-scaled version of the incident signal. Non-linear scattering media produce signals that cannot be produced by simple time-shifts, scaling, or summation of the signal incident to a scattering site. The phase of an ultrasound wave reflected from the boundary of a non-linear medium is altered in a manner that depends on the phase of the incident sound pulse. For example, consider the special case of two ultrasound pulses (k=2), where the phase difference between the two transmitted sound pulses differ by $$\frac{360°}{k} = \frac{360°}{2}$$

or 180 degrees. If the scattering site were purely linear then the received signal from each of the transmitted pulses would be the inverse of each other. These inverse signals, when averaged, would have a sum of zero. If, however, there are signals generated from a non-linear process within the media, then these signals will not be the inverse of each other and, consequently, will not sum to zero.

This non-linear property can be used to construct a system that looks at the non-linear regions within given media. For example, in one embodiment of this system, an image area is formed from three different sets of transmitted signals each differing in phase by 120 degrees. The linear reflections generated by these k=3 sets of excitation pulses will cancel each other, while the $k^{th}$ order non-linear components will not. This pulse cancellation allows an averaged set of raw received data, F(n, t), to be produced. A three-dimensional averaged set of raw received data, F(n,m,t), may also be produced where m is an element from a two-dimensional, or n×m transducer array. The data functionality is dependent on the channel (or transducer) number and time. This single set of averaged data can then be used to re-construct an image area. The image area reconstructed would represent the information generated from the third, or $k^{th}$, harmonic, generated from the scattering sites within the media.

DETAILED DESCRIPTION OF THE INVENTION

The present invention relates to the field of ultrasound imaging. This invention utilizes broad beam technology ($B^2$ Technology™) to perform image extraction of the non-linear elements of media under investigation. These media will hereinafter be referred to as media of interest. Broad beam technology defines an area under investigation at a given point in time, which is in contrast with a system utilizing a focused beam.

Figure 1:
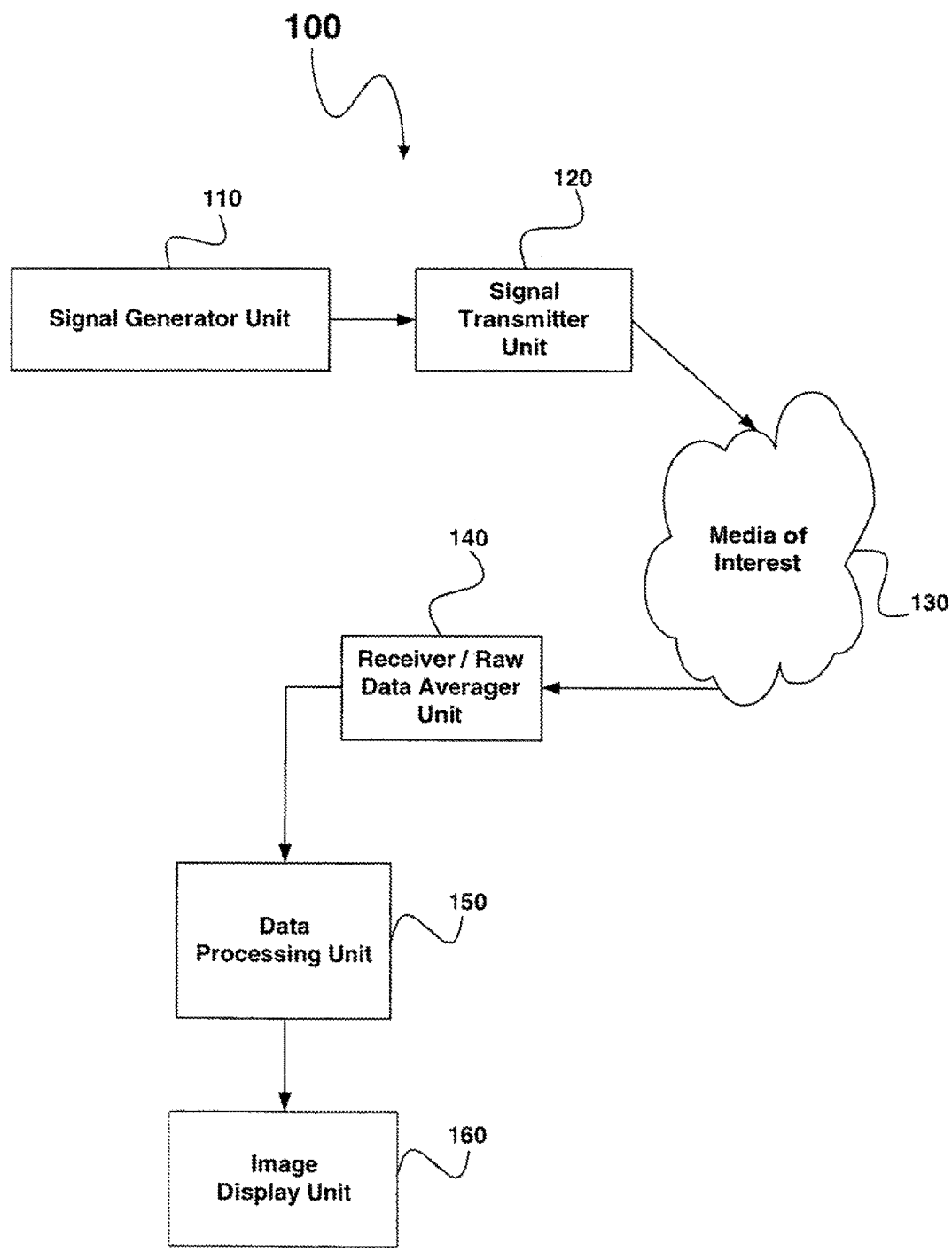
FIG. 1 is a schematic block diagram of an embodiment of an ultrasound imaging system using the present invention.

FIG. 1 is a block diagram of an embodiment of an ultrasound imaging system using the present invention. Imaging system 100 includes at least one signal generator unit 110, at least one signal transmitter unit 120, media of interest 130 to be imaged, at least one receiver and raw data averager unit 140 to capture signals received from the media of interest 130, and a data processing unit 150 for taking the averaged received signals and producing an area of image formation on an image display unit 160.

A signal generator unit 110 drives circuitry for a signal transmitter unit 120. The signal transmitter unit is shown and described in greater detail in FIG. 3.

A signal transmitter unit 120 transmits pulsed sets of ultrasonic energy into the media of interest 130. Echoes received from the media of interest 130 are stored in the receiver and raw data averager unit 140. Subsequent out-of-phase signals from the signal generator unit 110 pass through the signal transmitter unit 120, and are converted into pulsed sets of ultrasonic energy that travel to the media of interest 130. The media of interest 130 modifies the pulsed sets of ultrasonic energy. These modified pulsed sets of ultrasonic energy are received and averaged by the receiver and raw data averager unit 140. Data from these received pulsed sets are averaged in a data set as a function of channel number, n, and time, t. The averaged data sets are processed by the data processing unit 150 and displayed on an image display unit 160.

Figure 2:
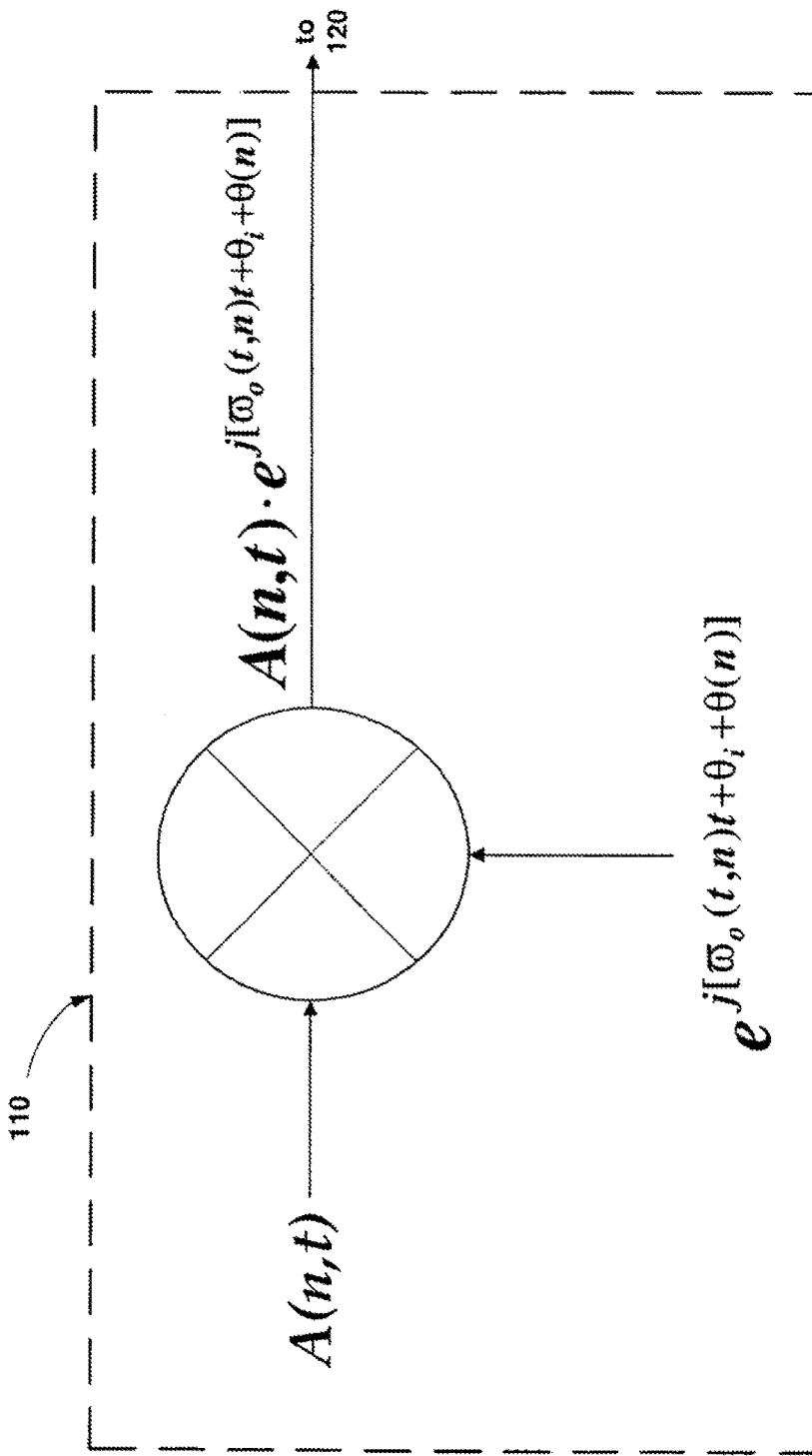
FIG. 2 shows an exemplary modification of one of a potential plurality of waveforms being modified.

FIG. 2 shows an exemplary modification of one of a potential plurality of waveforms being modified. This FIG. 2 example demonstrates how a signal generator unit 110 may modify a generated signal. For example, a stated modulation may be in the form of any combination of varying an amplitude, frequency, or pulse width of an unaffected input signal. These modulated signals will additionally vary in phase for a given pulse set. To produce a modulation, an envelope function, A(n,t), may be convolved with a sine wave, depicted by $e^{j[w_o(t,n)t+\theta_i+\theta(n)]}$ giving the final waveform A(n,t) $e^{j[w_o(t,n)t+\theta_i+\theta(n)]}$. In this waveform notation, n is the transducer element number, and i is a given pulse index (e.g., if a second harmonic is utilized, k=2, then i=1 . . . 2). The phase varies for different pulse sequences within a given pulse set and is indicated by the $\theta_i$ notation.

To illustrate the concept of phase variation, take an example where k is three. In this example, each pulse within a pulse set is varied in phase by $$\frac{360°}{k} \equiv \frac{360°}{3}$$

or 120°. A first pulse is generated with a 0° phase orientation, a second pulse is 120° out-of-phase with the first pulse, and a last pulse in the pulse set is 240° out-of-phase with respect to the first pulse. After the first pulse is transmitted and received, the second pulse is transmitted and received, and so on through the sequence. All information is tracked so that fundamental frequencies can be summed and eliminated, leaving primarily only harmonically generated echoes. Recall that harmonically generated echoes are produced by non-linear media.

Further, as an example, an envelope function, A(n,t), may be a Gaussian waveform. The transmitted signal may additionally be modulated as a chirped waveform (i.e., sweptfrequency modulation, a Fourier transform of which is still centered around the fundamental with a broader dispersion). Optionally, a digital waveform generator could be used in place of the convolution method shown in FIG. 2.

Figure 3:
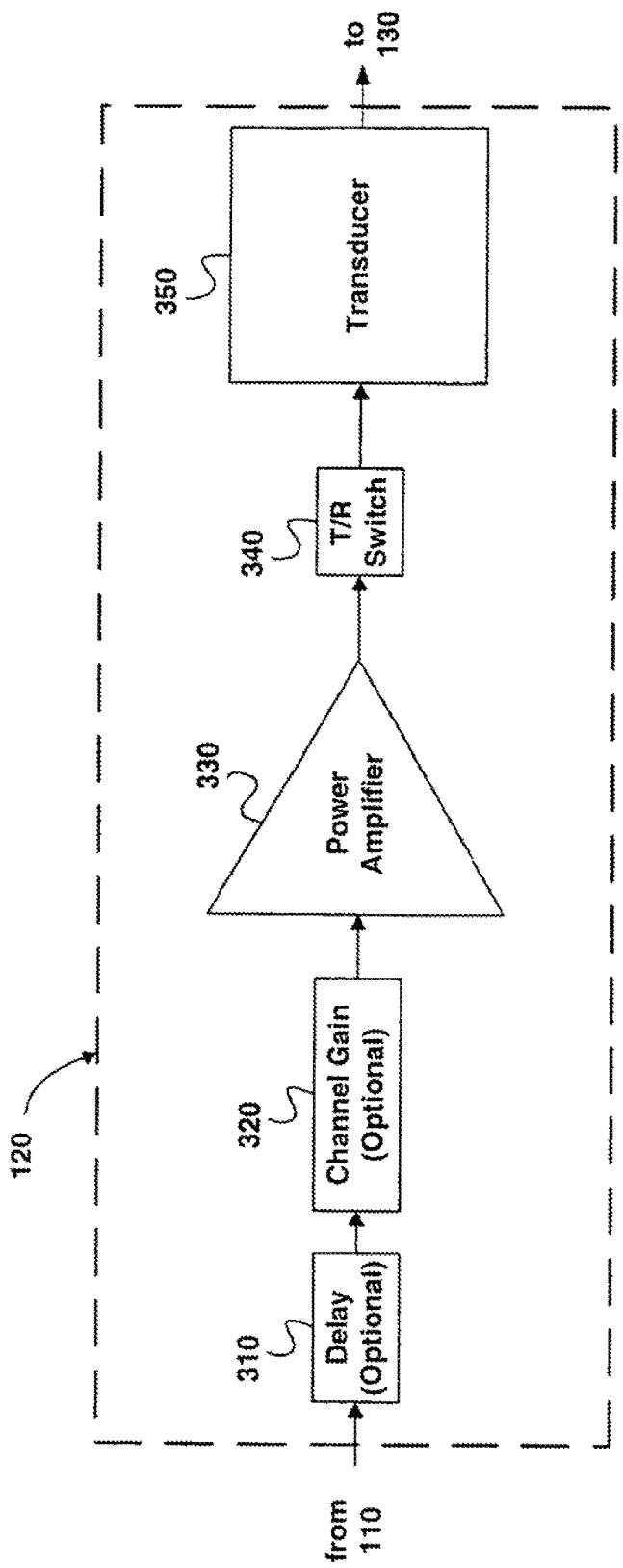
FIG. 3 shows an embodiment of a signal transmitter unit prior to signal delivery to media of interest.

FIG. 3 shows an embodiment of a signal transmitter unit 120 prior to signal delivery to media of interest. The signal transmitter unit 120 includes at least a power amplifier 330, a transmit/receive switch 340, and a first transducer 350. Optionally, a signal transmitter unit 120 may further include a delay circuit 310. The delay circuit 310 may be an analog or digital delay. Also, optionally, the signal transmitter unit 120 may include a channel gain unit 320 to drive the power amplifier 330 as a function of channel number and time. Additionally, the signal or pulse may be pulse-width modulated (not shown) to conserve power. Power conservation can become crucial in field applications of the system where battery power may be utilized.

Figure 4A:
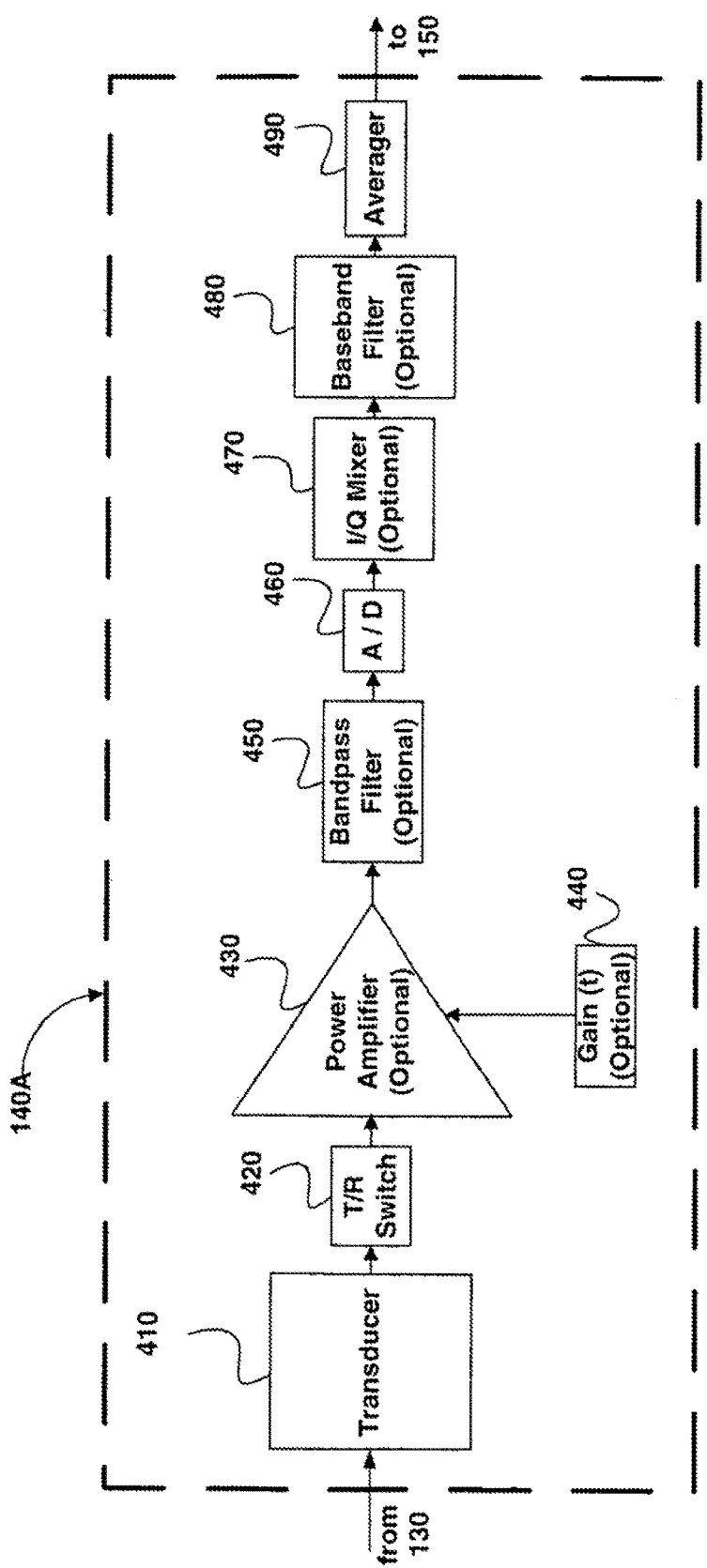
FIG. 4A shows an embodiment of a receiver and raw data averager unit.
Figure 4B:
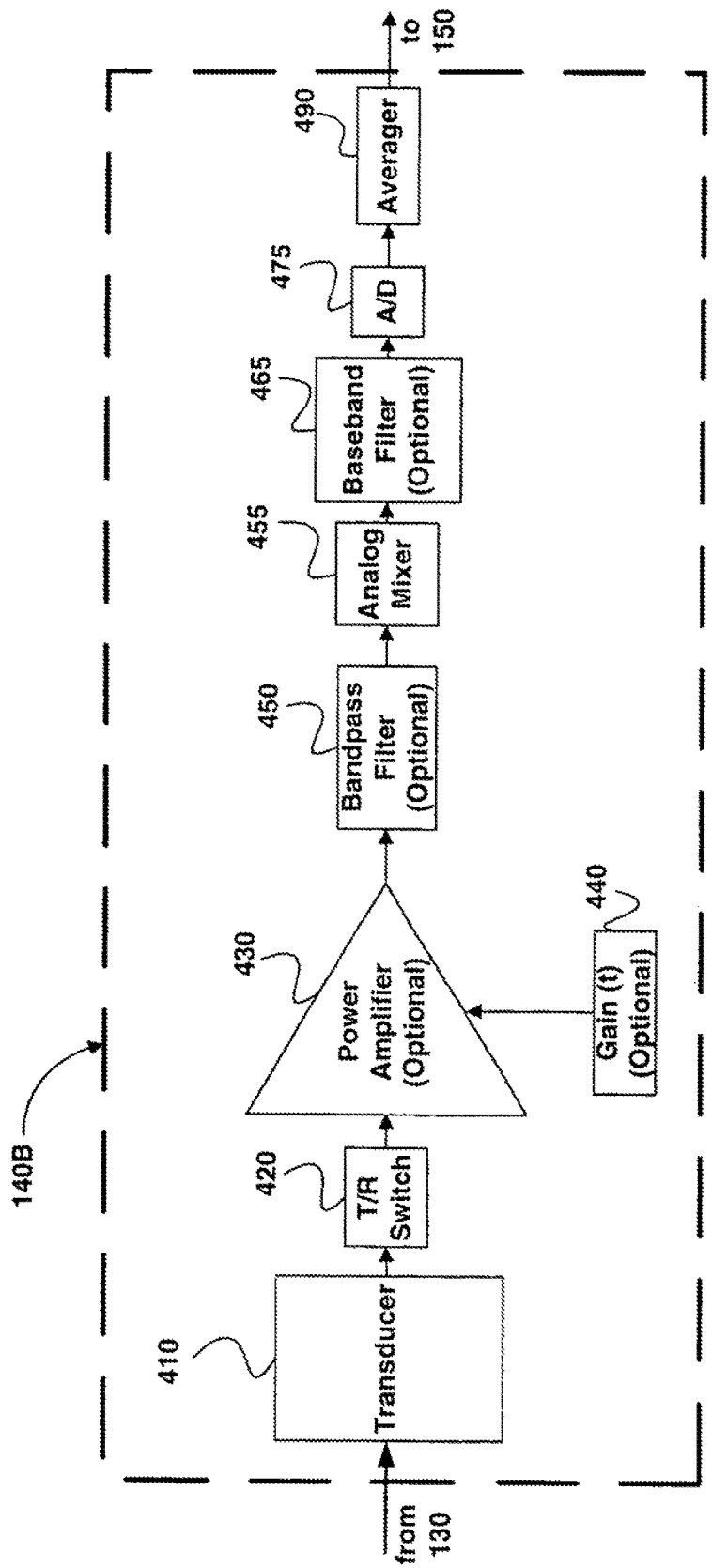
FIG. 4B shows an alternative embodiment of a receiver and raw data averager unit.

FIG. 4A shows one embodiment of a receiver and raw data averager unit 140. A second transducer 410 receives pulsed sets modified by media of interest 130. These received pulsed sets are transformed from ultrasonic energy into an electrical signal by the second transducer 410. A second transmit/receive switch 420 may be used to couple the electrical signals to the appropriate circuitry. In one embodiment, a second transducer 410 and a second transmit/receive switch 420 may be coincident or analogous units to the first transducer 350 and first transmit/receive switch 340 shown in FIG. 3. A second power amplifier 430 may be added and controlled as a function of time by gain control unit 440. The output of power amplifier 430 sends an amplified signal to an optional bandpass filter 450. The bandpass filter 450 may be used, among other things, to reduce or eliminate extraneous noise. FIGS. 4A and 4B share the same component layout up to and including bandpass filter 450, where thereafter they diverge thereby exemplifying alternate embodiments.

The electrical signal of the FIG. 4A embodiment is coupled to a first analog-to-digital (A/D) converter 460, and may continue into an optional in-phase and quadrature (I/Q) mixer 470, which produces a single side-band signal, optional first baseband filter 480, and to an averager 490. The optional first baseband filter acts to reduce or eliminate any fundamental frequency from the signals received from the original pulse sets, leaving primarily harmonically generated signals. One purpose of the averager is to provide a point-by-point arithmetic average of the received electrical signals. Mathematically, this arithmetic average may be expressed as $$F(n, t) = \sum_{i=1}^{k} \frac{R_i(n, t)}{k},$$

where the received signal, $R_i$, is summed for each element of the transmit cycle as a function of channel number and time to correlate with the original transmitted pulse, i. All other components in the signal path are of types commonly known to one of ordinary skill in the art.

FIG. 4B shows an alternative embodiment of a receiver and raw data averager unit. Recall FIGS. 4A and 4B share the same component layout through and including the optional bandpass filter 450. From the point of this optional bandpass filter 450, the signal of the FIG. 4B embodiment is further coupled to an analog mixer 455, an optional second baseband filter 465, a second analog-to-digital converter 475, and an averager 490.

Figure 5:
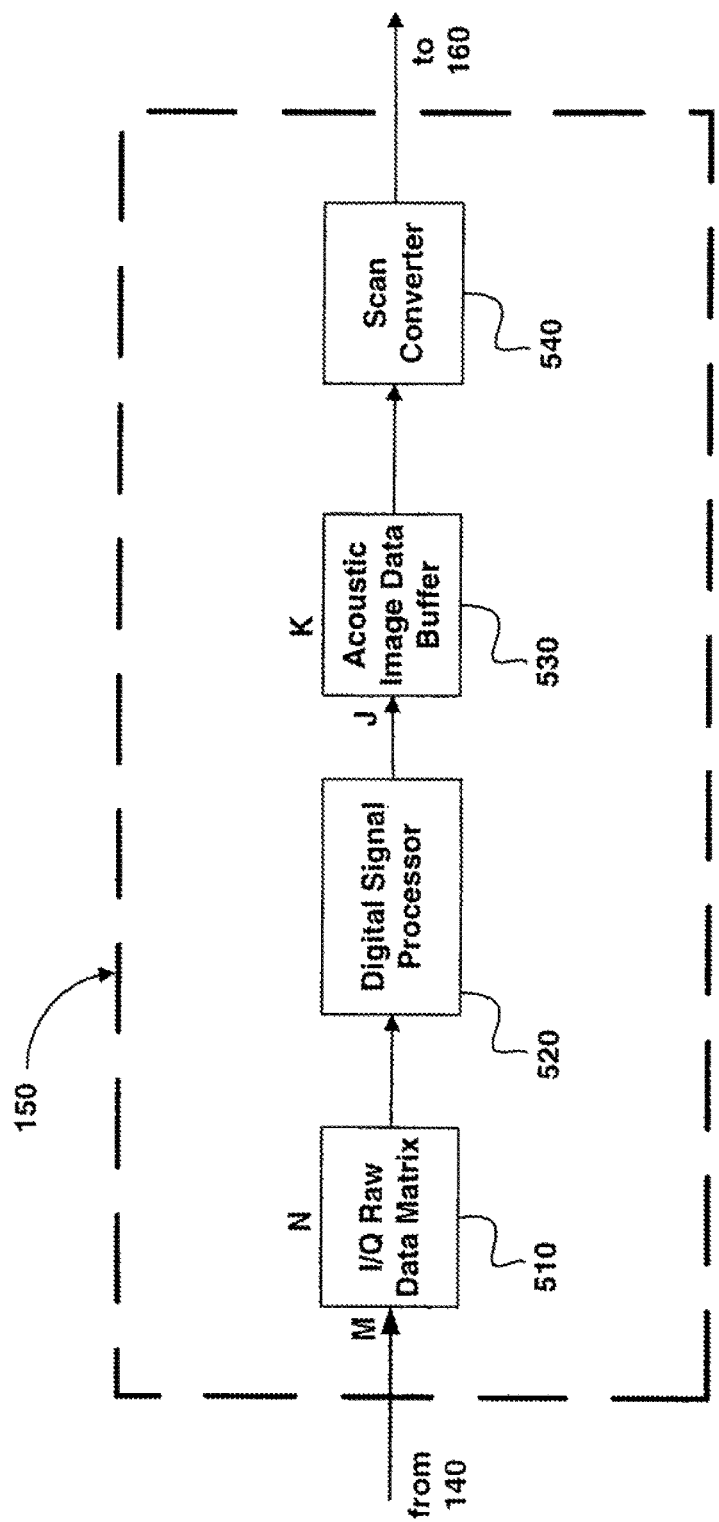
FIG. 5 shows an embodiment of a data processing unit.

FIG. 5 shows an embodiment of the data processing unit 150. Here, data processing unit 150 receives averaged data from the receiver and raw data averager unit 140. The averaged data are input to the data processing unit 150 and received at I/Q raw data matrix 510, which stores the averaged data in an M×N area array, where M is the number of samples (1 to 10,000 samples is an exemplary number) and N is the number of elements×2 (both in-phase and quadrature). These averaged data are fed into a digital signal processor (DSP) 520, which reconstructs the raw data into an area of acoustic image. An exemplary reconstruction equation may take the form of $$I(r, \varphi) = \sum_{i=1}^{k} a_i(r, \varphi) \cdot e^{j\theta_i(r,\varphi)} \cdot F[i, t_i(r, \varphi)].$$

In this equation $a_i$ indicates an aperture function, r refers to a radial distance from a transducer center at a given angle $\varphi$, and the function F is an averaged set of raw received data. The digital signal processor 520 functions could be achieved in any number of ways, For example, in an alternative embodiment, a properly designed application-specific integrated circuit (ASIC) could be used in place of the digital signal processor 520. These converted data in polar coordinates are saved in an acoustic image data buffer 530 in a J×K matrix (where J is the number of range samples and K is the number of angular samples). At this point, the data are still a function of a distance, r, from the transducer at a given angle, $\varphi$. This could also be accomplished in a Cartesian coordinate system. The acoustic image data buffer 530 allows the data to be stored until needed by scan converter 540. The I(r,$\varphi$) image data are converted into a reconstructed image in Cartesian coordinate data I(x,y) through the use of an r-$\varphi$ scan converter 540. An r-$\varphi$ scan converter is well known in the art and typically converts two-dimensional data from polar to Cartesian coordinates by means of the conversion, $$x = r \cos(\varphi) \text{ and } y = r \sin(\varphi).$$

Output from the data processing unit 150 produces an image area I(x,y) corresponding to an area irradiated by pulsed sets of ultrasonic energy. These converted I(x,y) data may be displayed on image display unit 160. Image display unit 160 may be any visual display such as, but not limited to, a computer monitor, flat-panel or liquid-crystal display, cathode-ray tube (CRT), or the like.

From the description of the preferred embodiments of the process and apparatus set forth supra, it will be apparent to one of ordinary skill in the art that variations and additions to the embodiments can be made without departing from the principles of the present invention. For example, it could be easy to envision a system whereby an entire three-dimensional (3D) volume could be displayed at once as opposed to a two-dimensional area. This three-dimensional embodiment may be accomplished by holography or some other means. It would be an obvious extrapolation from the tenets of the two-dimensional system presented herein to construct a three-dimensional apparatus.

What is claimed is:

1. A system for three-dimensional ultrasonic imaging, comprising:
   a signal generator unit that generates out-of-phase pulses for ultrasonic imaging, wherein the signal generator unit is configured to:

generate a first pulse for ultrasonic imaging at a first phase; and convolve the first pulse with an envelope function to generate a second pulse that is out-of-phase with respect to the first pulse based on a number of pulses in a pulse set including the first pulse and the second pulse;

a signal transmitter unit coupled to the signal generator unit and that converts the out-of-phase pulses into out-of-phase acoustical pulses and that transmits the out-of-phase acoustical pulses into media of interest;

a receiver that receives, via at least two channels, return acoustical pulses corresponding to the out-of-phase acoustical pulses modified by non-linear elements of the media of interest;

an acoustical raw channel data averager unit that averages the return acoustical pulses as a function of a channel number of the at least two channels and time to form a combined average signal and stores raw, averaged received acoustical pulse channel data corresponding to the combined average signal;

a data processing unit coupled to the receiver and the raw channel data averager unit, wherein the data processing unit constructs two dimensional image data from the raw, averaged received acoustical pulse channel data, and derives three dimensional image data from the two dimensional image data; and an image display unit that displays the three dimensional image data.

2. The system of claim 1, wherein the signal transmitter unit comprises:

a power amplifier that amplifies the out-of-phase pulses to form amplified out-of-phase pulses, and a transmit/receive switch that selectively couples the amplified out-of-phase pulses to a transducer for transmission.

3. The system of claim 2, further comprising a digital delay circuit coupled between the signal generator unit and the power amplifier to delay the out-of-phase pulses.

4. The system of claim 2, further comprising an analog delay circuit coupled between the signal generator unit and the power amplifier to delay the out-of-phase pulses.

5. The system of claim 2, further comprising a channel gain circuit coupled between the signal generator unit and the power amplifier to drive the power amplifier as a function of the channel number and the time.

6. The system of claim 1, wherein the receiver and the acoustical raw channel data averager unit comprise:

a transducer that receives the return acoustical pulses, a transmit/receive switch that couples the transducer to an analog-to-digital converter that digitizes the return acoustical pulses to form digitized return acoustical pulses, and an averager that averages the digitized return acoustical pulses to form the raw, averaged received acoustical pulse channel data.

7. The system of claim 6, wherein the receiver and the raw channel data averager unit further comprise:

a power amplifier that amplifies the return acoustical pulses to form amplified pulses;

a bandpass filter that filters the amplified pulses to form filtered pulses; and a baseband filter that further filters the filtered pulses.

8. The system of claim 6, wherein the receiver and the raw channel data averager unit further comprise an in-phase and quadrature mixer coupled between the power amplifier and the acoustical raw channel data averager unit, the mixer producing a side-band signal.

9. The system of claim 1, wherein the signal transmitter unit, the receiver, and the acoustical raw channel data averager unit communicate with a transducer that transmits out-of-phase pulses and that receives the return acoustical pulses.

10. The system of claim 1, wherein the data processing unit comprising:

an in-phase and quadrature mixer that down converts the return acoustical pulses from a first frequency to a second frequency to produce a side-band signal, a digital signal processor that constructs the two dimensional image data based on the side-band signal, an acoustic image data buffer that buffers the two dimensional image data to form buffered two dimensional image data, and a scan converter that converts the buffered two dimensional image data from a first coordinate system to a second coordinate system for display on the image display unit.

11. The system of claim 1, wherein the data processing unit comprises:

an in-phase and quadrature mixer that down converts the return acoustical pulses from a first frequency to a second frequency to produce a side-band signal, an application specific integrated circuit that constructs the two dimensional image data based on the side-band signal to derive the three dimensional image data, an acoustic image data buffer that buffers the three dimensional image data to form buffered three dimensional image data, and a scan converter that converts the buffered three dimensional image data from a first coordinate system to a second coordinate system for display on the image display unit.

12. A method for performing three-dimensional ultrasonic imaging comprising:

generating out-of-phase pulses including a first pulse and a second pulse formed by convolving the first pulse with an envelope function to generate the second pulse that is out-of-phase with respect to the first pulse based on a number of pulses in a pulse set including the first pulse and the second pulse;

converting the out-of-phase pulses into out-of-phase acoustical pulses;

transmitting the out-of-phase acoustical pulses into media of interest;

receiving, via at least two channels, return acoustical pulses corresponding to the out-of-phase acoustical pulses modified by non-linear elements of the media of interest;

averaging the return acoustical pulses as a function of a channel number of the at least two channels and time to form a combined average signal, storing the raw, averaged received acoustical pulse channel data corresponding to the combined average signal;

generating a series of two dimensional image data based on the raw, averaged received acoustical pulse channel data; and constructing three-dimensional image data from the series of two dimensional image data.

13. The method of claim 12, wherein the out-of-phase pulses are modulated by a change in amplitude.

14. The method of claim 12, wherein the out-of-phase pulses are modulated by a change in frequency.

15. The method of claim 12, wherein the out-of-phase pulses are modulated by a change in pulse width.

16. The method of 12, wherein the envelope function is a Gaussian waveform.

17. The method of claim 12, wherein the envelope function is a chirped waveform.

18. The method of claim 12, wherein a phase of the out-of-phase pulses varies by 360 degrees divided by an integral denominator that is equal to an integral number of the out-of-phase pulses.

19. The method of claim 12, further comprising: displaying all of the three-dimensional image data at once.

20. A method for performing ultrasonic imaging, comprising:
    generating out-of-phase pulses that includes a first pulse and a second pulse, the second pulse generated by convolving the first pulse with an envelope function to generate the second pulse that is out-of-phase with respect to the first pulse based on a number of pulses in a pulse set including the first pulse and the second pulse;
    converting the out-of-phase pulses into out-of-phase acoustical pulses;
    transmitting the out-of-phase acoustical pulses into media of interest;
    receiving return pulses from the media of interest corresponding to the out-of-phase pulses modified by non-linear elements of the media of interest;
    averaging acoustical pulse channel data associated with the return pulses received via at least two channels as a function of a channel number of the at least two channels and time to form combined average acoustical pulse channel data,
    constructing two dimensional image data from the return pulses and the combined average acoustical pulse channel data;
    deriving three dimensional image data from the two dimensional image data; and
    displaying all of the data corresponding to the three-dimensional image data at once.

21. A system for generating a three-dimensional ultrasonic image comprising:
    a signal generator unit that generates out-of-phase electrical pulses including a first pulse and a second pulse, wherein the second pulse is generated based on a number of pulses in a pulse set including the first pulse and the second pulse by convolving the first pulse with an envelope function;
    a signal transmitter unit coupled to the signal generator unit that converts the out-of-phase electrical pulses into out-of-phase acoustical pulses and transmits the out-of-phase acoustical pulses into a media of interest;
    a receiver that receives, via at least two channels, return acoustical pulses corresponding to out-of-phase electrical pulses modified by non-linear elements of the media of interest;
    an acoustical raw data channel averager unit that averages the return acoustical pulses as a function of a channel number of the at least two channels and time to form a combined average signal, and stores raw, averaged received acoustical pulse channel data corresponding to the combined average signal,
    a data processing unit coupled to the acoustical raw data channel averager unit, wherein the data processing unit constructs a two dimensional series of data from the raw, averaged received acoustical pulse channel data; and
    an image display unit that receives an output from the data processing unit and displays acoustic image data based on the two dimensional series of data.

22. The system of claim 21, wherein the signal generator modulates the out-of-phase pulses such that they are essentially sinusoidal.

23. The system of claim 21, wherein the signal transmitter unit comprises:
    a power amplifier that amplifies the out-of-phase pulses to form amplified out-of-phase pulses, and
    a transmit/receive switch that selectively couples the amplified out-of-phase pulses to a transducer for transmission.

24. The system of claim 23, further comprising a digital delay circuit coupled between the signal generator unit and the power amplifier to delay the out-of-phase acoustical pulses.

25. The system of claim 23, further comprising an analog delay circuit coupled between the signal generator unit and the power amplifier to delay the out-of-phase acoustical pulses.

26. The system of claim 23, further comprising a channel gain circuit coupled between the signal generator unit and the power amplifier to drive the power amplifier as a function of the channel number and the time.

27. The system of claim 21, wherein the receiver and the acoustical raw channel data averager unit comprise:
    a transducer that receives the return acoustical pulses,
    a transmit/receive switch that couples the transducer to an analog-to-digital converter that digitizes the return acoustical pulses to form digitized return acoustical pulses, and
    an averager that averages the digitized return acoustical pulses to form the two dimensional series of data as a function of the channel number and the time.

28. The system of claim 27, wherein the receiver and the raw channel data averager unit further comprise:
    a power amplifier that amplifies the return acoustical pulses to form amplified pulses;
    a bandpass filter that filters the amplified pulses to form filtered pulses; and
    a baseband filter that further filters the filtered pulses.

29. The system of claim 27, wherein the receiver and the raw channel data averager unit further comprise an in-phase and quadrature mixer coupled between the power amplifier and the acoustical raw channel data averager unit, the mixer producing a side-band signal.

30. The system of claim 21, wherein the receiver and the acoustical raw channel data averager unit store the return acoustical pulses received to form a series of return pulses.

31. The system of claim 21, wherein the receiver and the acoustical raw channel data averager unit construct a set of averaged raw received data.

32. The system of claim 21, wherein the signal transmitter generator unit, the receiver, and the acoustical raw channel data averager unit communicate with a transducer that transmits the out-of-phase acoustical pulses and receives the return acoustical pulses.

33. The system of claim 21, wherein the data processing unit comprises:
    an in-phase and quadrature mixer that down converts the return acoustical pulses from a first frequency to a second frequency to produce a side-band signal,
    a digital signal processor that constructs the two dimensional series of data based on the side-band signal, an acoustic image data buffer that buffers the two dimensional series of data to form buffered two dimensional image data, and a scan converter that converts the buffered two dimensional image data from a first coordinate system to a second coordinate system for display on the image display unit.

34. The system of claim 21, wherein the data processing unit comprises:

an in-phase and quadrature mixer that down converts the return acoustic pulses from a first frequency to a second frequency to produce a side-band signal, an application specific integrated circuit that constructs the two dimensional series of data based on the sideband signal, an acoustic image data buffer that buffers the two dimensional series of data, and a scan converter that converts the two dimensional series of data received from the acoustic image data buffer from a first coordinate system to a second coordinate system for display on the image display unit.

35. The system of claim 33, wherein the acoustic image data buffer stores two-dimensional image data in order to create a three-dimensional image.

36. The system of claim 21, wherein the data processing unit constructs three-dimensional image data from the two dimensional series of data.

37. The system of claim 21, wherein the data processing unit outputs a three-dimensional image to the image display unit.

38. A system for ultrasonic imaging, comprising:

a signal generator unit for generating out-of-phase acoustical pulses including a first acoustical pulse and a second acoustical pulse, the second acoustical pulse generated by convolving the first pulse with an envelope function to generate the second acoustical pulse that is out-of-phase with respect to the first acoustical pulse based on a number of pulses in a pulse set including the first acoustical pulse and the second acoustical pulse;

a signal transmitter unit coupled to the signal generator unit for transmitting the out-of-phase pulses into media of interest;

a receiver for receiving, via at least two channels, the return acoustical pulses corresponding to the out-of-phase pulses modified by non-linear elements of the media of interest;

an acoustical raw channel data averager unit that averages the return acoustical pulses as a function of a channel number of the at least two channels and time to form a combined average signal, based on a point-by-point arithmetic average of the return acoustical pulses; and a data processing unit coupled to the receiver and the raw channel data averager unit, the data processing unit constructing an area of acoustic image having at least two dimensions based on the combined average signal.

39. The system of claim 38, wherein the signal generator unit is a digital waveform generator.

40. The system of claim 38, wherein the signal generator unit modulates an amplitude of at least two out-of-phase sine waves to produce the out-of-phase pulses.

41. The system of claim 38, wherein the signal generator unit modulates a frequency of at least two out-of-phase sine waves, which produce the out-of-phase pulses.

42. The system of claim 38, wherein the signal generator unit modulates a pulse width of at least two out-of-phase sine waves, to produce the out-of-phase pulses.

43. The system of claim 38, wherein the envelope function is a Gaussian waveform.

44. The system of claim 38, wherein the envelope function is a chirped waveform.

45. The system of claim 38 wherein the signal transmitter unit comprises a power amplifier that amplifies the out-of-phase pulses to form amplified out-of-phase pulses, and a transmit/receive switch that selectively couples the amplified out-of-phase pulses to a transducer for transmission.

46. The system of claim 45, further comprising a digital delay circuit configured to delay the transmission of the out-of-phase pulses into media of interest.

47. The system of claim 45, further comprising an analog delay circuit configured to delay the transmission of the at least two out-of-phase pulses into media of interest.

48. The system of claim 45, further comprising a channel gain circuit to drive the power amplifier.

49. The system of claim 38, wherein the out-of-phase pulses are alternately transmitted by the signal transmitter unit to produce a pulse set.

50. The system of claim 38, wherein the receiver and the raw channel data averager unit comprise:

a transducer that receives the return acoustical pulses, a transmit/receive switch that couples the transducer to an analog-to-digital converter that digitizes the return acoustical pulses to form a digitized return acoustical pulses, and an averager that averages the digitized return acoustical pulses to form an average combined data set as a function of the channel number and the time.

51. The system of claim 50, wherein the receiver and the raw channel data averager unit further comprise:

a power amplifier that amplifies the return acoustical pulses to form amplified pulses, a bandpass filter that filters the amplified pulses to form filtered pulses, and a baseband filter that filters the filtered pulses.

52. The system of claim 45, wherein the receiver and the raw channel data averager unit further comprise:

an in-phase and quadrature mixer coupled between the power amplifier and the averager and that produces a single side-band signal.

53. The system of claim 38, wherein the signal generator unit, the receiver, and the acoustical raw channel data averager unit communicate with a transducer that transmits the out-of-phase pulses and that receives the return pulses.

54. The system of claim 38, wherein the data processing unit comprises:

an in-phase and quadrature mixer that down converts the return acoustical pulses from a first frequency to a second frequency to produce a side-band signal, a digital signal processor that constructs the area of the acoustic image based on the sideband signal, an acoustic image data buffer that buffers the constructed area of the acoustic image to form a buffered area of the acoustic image, and a scan converter that converts the buffered area of the acoustic image from a first coordinate system to a second coordinate system for display.

55. The system of claim 38, wherein the data processing unit comprises:

an in-phase and quadrature mixer that down converts the return acoustical pulses from a first frequency to a second frequency to produce a side-band signal, an application specific integrated circuit that constructs the area of the acoustic image based on the side-band signal, an acoustic image data buffer that buffers the constructed area of the acoustic image to form a buffered area of the acoustic image, and a scan converter that converts the buffered area of the acoustic image from a first coordinate system to a second coordinate system for display.

56. The system of claim 38, further comprising an image display unit coupled to the data processing unit and that displays the area of the acoustic image.

57. The system of claim 56, wherein the image display unit is a computer monitor.

58. The system of claim 56, wherein the image display unit is a flat-panel display.

59. The system of claim 56, wherein the image display unit is a liquid-crystal display.

* * * * *